US008348842B1

(12) United States Patent
Osorio et al.

(10) Patent No.: US 8,348,842 B1
(45) Date of Patent: *Jan. 8, 2013

(54) METHOD AND SYSTEM FOR IMPLANTABLE GLUCOSE MONITORING AND CONTROL OF A GLYCEMIC STATE OF A SUBJECT

(75) Inventors: Ivan Osorio, Leawood, KS (US); Mark G. Frei, Lawrence, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/135,375

(22) Filed: Jul. 1, 2011

Related U.S. Application Data

(63) Continuation of application No. 12/802,009, filed on May 27, 2010, now Pat. No. 7,988,630, which is a continuation of application No. 11/128,600, filed on May 13, 2005, now Pat. No. 7,727,147.

(60) Provisional application No. 60/571,268, filed on May 14, 2004.

(51) Int. Cl.
*A61B 5/00* (2006.01)
*A61B 5/05* (2006.01)

(52) U.S. Cl. .................. 600/365; 600/345; 600/347

(58) Field of Classification Search .................. 600/345, 600/347, 365; 604/48, 65, 500, 502–504, 604/890.1, 891.1
See application file for complete search history.

(56) References Cited

U.S. PATENT DOCUMENTS

| | | | |
|---|---|---|---|
| 5,680,858 A | 10/1997 | Hansen et al. | |
| 6,524,256 B2 | 2/2003 | Schaldach et al. | |
| 6,895,263 B2 | 5/2005 | Shin et al. | |
| 7,727,147 B1 | 6/2010 | Osorio et al. | |
| 2002/0183604 A1 | 12/2002 | Gowda et al. | |
| 2003/0130616 A1 | 7/2003 | Steil et al. | |
| 2004/0204744 A1 | 10/2004 | Penner et al. | |
| 2005/0159800 A1 | 7/2005 | Marshall et al. | |

*Primary Examiner* — Patricia Mallari
*Assistant Examiner* — Christian Jang
(74) *Attorney, Agent, or Firm* — Donald R. Schoonover

(57) ABSTRACT

A method and system for monitoring and/or controlling a glycemic state of a subject, comprising a housing device having one or more chambers, extendable and retractable sensors, extendable and retractable catheters, insulin reservoir, neuroprotective agent reservoir, release mechanism for releasing insulin and neuroprotective agent into the subject, and a control mechanism with a processor for receiving and analyzing outputs from the sensors and for controlling the release mechanism, a clock mechanism for providing logging and/or circadian information to the processor.

4 Claims, 2 Drawing Sheets

METHOD AND SYSTEM FOR IMPLANTABLE GLUCOSE MONITORING AND CONTROL OF A GLYCEMIC STATE OF A SUBJECT

CROSS REFERENCE TO RELATED APPLICATION

This application is a continuation of application Ser. No. 12/802,009 filed May 27, 2010, now U.S. Pat. No. 7,988,630, issued Aug. 2, 2011; which is a continuation of application Ser. No. 11/128,600 filed May 13, 2005, now U.S. Pat. No. 7,727,147, issued Jun. 1, 2010; which claims the priority of Provisional Application No. 60/571,268 filed May 14, 2004, all of which are incorporated herein by reference.

BACKGROUND OF THE INVENTION

1. Field of the Invention

The present invention is in the field of medical devices and the methods for use thereof. More particularly it relates to systems and methods for monitoring and controlling the glycemic state of a subject to avoid undesirable states such as those corresponding to hyperglycemia, hypoglycemia, and neuroglycopenia.

2. Description of the Related Art

Tight control of blood glucose levels currently offers the best chance of reducing the long-term complications of diabetes mellitus. However, attempts to maintain near-normal glycemia often increase the risk of hypoglycemia. Although patients may perform self-monitored blood glucose (SMBG) tests four or more times per day, many episodes of hypoglycemia go undetected due to the absence of overt symptoms or because they occur at night, when glucose testing is rare. As a result, hypoglycemia is responsible for dramatic economic costs and many avoidable deaths each year.

Implantable glucose sensors are inserted beneath the skin or inside a blood vessel. This technology has been in development for quite some time, but the first prior art device only became commercially available in the past few years. Such monitors, which rely on advances in chemical sensors and biocompatible materials, are a step toward the ultimate goal: a glucose sensor that can be connected directly with an insulin delivery system to provide an artificial pancreas, the organ that controls blood glucose levels in the body.

The aforesaid prior art device can only operate for up to three days, which is certainly not a permanent solution, but one that yields enough information to improve a person's treatment regimen. The device records glucose levels for a healthcare professional to view during the patient's next office visit. A user performs two to four finger-prick blood glucose measurements to calibrate the device, which then supplies readings at five-minute intervals. Clinical researchers report identifying low glucose levels at night and high glucose after a meal that were previously unobserved by periodic pinpricks.

The aforesaid prior art device is an example of an enzymatic electrochemical sensor. In brief, an enzyme, commonly referred to as glucose oxidase, is fixed to an electrode and catalyzes the conversion of glucose into gluconic acid and hydrogen peroxide. The hydrogen peroxide then reacts at the sensing electrode, which is typically biased at 0.6 V, resulting in a measurable electric current.

Generally, implantable sensors can be categorized by the site of implantation and the method of measuring glucose. Subcutaneous sensors are inserted beneath the skin through a needle and measure glucose in interstitial fluid, the liquid between the cells. Other sensors are surgically affixed to the inside of a large vein and measure glucose in blood. Most sensors, like the aforesaid prior art device, employ an enzymatic conversion step to turn glucose into a chemical signal that can be easily measured electrochemically or optically.

The main challenge in developing a glucose sensor for implantation beneath the skin or in a vein is to maintain the sensors performance when it is exposed to the inside of the body over long periods of time. Almost without exception, interactions with the body cause a decrease in sensor sensitivity. For example, the body's immune system inevitably launches an attack and tries to encapsulate the sensor in protein. The glucose-blocking barrier thus created blunts sensor sensitivity and lengthens response time.

In addition, the body's warm, electrolytic environment corrodes metal electrodes and can inactivate enzymes, which leads to loss of measurement sensitivity and stability. Movement by a person wearing the device can create artifacts and noise that decrease sensitivity and specificity to glucose signals and also produce mechanical stresses that affect stability.

Many other interactions with the body's environment must also be taken into consideration. For instance, substances such as vitamin C and acetaminophen may react at the electrode, creating spurious signals. Such chemicals can also destroy hydrogen peroxide before it can react at the electrode, thus providing spurious results. To minimize this effect, many implantable systems include membranes that keep these substances away from the sensor.

Another problem is that when glucose levels are high, oxygen may become the limiting reactant in the electrochemical sensing scheme that prior art devices utilize. The result is signal saturation and a limited system operating range. To combat this drawback, some investigators have introduced membranes that limit the amount of glucose that reaches the sensor, or they eliminate the need for oxygen by using sensing schemes that rely on alternative reactions.

Still another method for defending against attacks by the body is microdialysis. In this technique, dialysis tubing, constructed from a material that allows only small molecules to pass therethrough, is implanted under the skin. A special fluid is pumped through the tube into which glucose diffuses. The fluid is then collected and measured with an external sensor. This strategy prevents proteins from encasing the sensor.

The design of the aforesaid prior art device addresses some of the destructive interactions with the body. It is built on a flexible substrate in order to minimize the effects of motion and to fit more comfortably in the patient. The sensor is also coated with a biocompatible polyurethane to minimize the immune system's response.

Besides the subcutaneous types, some fully implantable glucose measurement systems are currently presently under development. These systems have the ambitious goal of providing continuous blood glucose measurements for several years and interfacing with an implantable insulin pump. The hoped for result is closed-loop control of glucose levels—in effect, an artificial pancreas.

Limitations of the prior art which are relevant to the present invention include the following:

(1) Existing glycemic control and delivery methods/systems do not mimic the anatomo-physiologic process of whole body glucose metabolism and regulation, including route and mode, rate and timing of insulin delivery and number and location of putative glucose biosensors. Existing methods/systems do not take into account the fact that there is no compartment in the body at which all glucose is at the same concentration, not even in circulating blood plasma glucose. Models of glucose metabolism, that include the effects of insulin based on assumptions of concentration homogeneity upon which existing systems/methods are based, cannot be entirely accurate.

(2) The prevailing concept, that only three key elements— (i) a safe and reliable insulin delivery device, (ii) an accurate glucose-sensing unit, and (iii) a control system that modulates insulin delivery according to blood glucose levels, variation, and trends—are required for the development of an artificial Beta-cell, is correct but overly simplistic, as it ignores several important facts:

(a) blood glucose alone does not suffice to determine a hypoglycemic (or hyperglycemic) threshold and/or state;

(b) plasma glucose concentration alone is not a satisfactory, fully reliable indicator of neuroglycopenia (neurologic dysfunction), which is the most serious potential complication of hypoglycemia;

(c) the decisions and procedures for glycemic control in commercially available systems are entirely in the hands of the diabetic person who may suffer from hypoglycemic unawareness, which makes them incapable of using the control method or system to correct this serious and potentially harmful situation.

(3) Prior art does not adequately incorporate into glucose control models or strategies the relative or partial dependency of glucose concentration at time, $t_0$, upon its concentration at a previous time, $t_1$.

(4) Glucose regulation is not under the exclusive control of insulin and the glucoregulatory response becomes either blunted or absent in type I diabetics at some point during the course of the illness. Even a single bout of hypoglycemia can significantly lower the threshold level of glucose required to initiate hypoglycemic awareness and the counter-regulatory response, causing hypoglycemia to be more serious and more likely to recur. Existing systems/methods do not take this into account.

(5) Prior art does not provide means of automatically protecting the brain from the deleterious effects of hypoglycemia on selectively vulnerable neuronal populations.

(6) The benefits of continuous subcutaneous insulin infusion, as performed in prior art systems, are contingent upon the subject's motivation, capacity to be educated, and ability to comply with complex instructions and procedures. This limits its applicability and usefulness, underscoring the need for a fully automated system.

(7) Continuous subcutaneous insulin infusion lacks the necessary reactivity to properly control/adjust insulin dose and the rate of release.

(8) Subcutaneous insulin absorption is unpredictable.

(9) Current systems suffer from inability to continuously and rapidly regulate or tune insulin delivery according to fluctuations in blood glucose concentrations.

(10) Glucose sensor performance degrades over time. For example, the body's immune system tries to encapsulate the sensor in protein, resulting in reduced sensor sensitivity and lengthened response time.

(11) Many glucose monitors are based on indirect measurements (e.g., enzymatic reactions). Other substances (besides glucose) may cause spurious readings in glucose sensors (e.g., Vitamin C and acetaminophen, or substances that react with hydrogen peroxide). Also some of these reactions require oxygen that may not be present in sufficient quantities to accurately complete the necessary reaction.

(12) Sensing processes may result in unwanted byproducts.

(13) Certain types of metal electrodes corrode, reducing sensitivity and stability.

(14) Electrode readings may be subject to movement-induced artifacts and other associated measurement noise that adversely affects sensitivity and specificity. Moreover, certain system designs may be prone to failure due to mechanical stresses and sensor movement.

(15) Some prior art systems use an external sensor to analyze acquired fluid (e.g. using microdialysis) which are inconvenient and have associated stigma for the user.

(16) Sensors placed in the blood stream may be prone to undesirable clotting or blood flow perturbations.

(17) Single sensor systems are more prone to failure than multiple sensor systems and are unable to accurately quantify complex glucose-insulin kinetics.

SUMMARY OF THE INVENTION

The improvements of the present invention include a method and system for monitoring or control of glycemic state of a subject comprising at least one housing device having one or more sensors, each capable of producing a sensor output; a reservoir containing insulin, the reservoir having a output port; an injection mechanism configured to controllably inject insulin through the output port, and a control mechanism configured to receive and analyze at least one sensor output from the one or more sensors and to responsively control the quantity of insulin injected through the output port by the injection mechanism; wherein the at least one housing device is at least partially embedded within, or affixed to, a tissue of the subject such that at least one of the one or more sensors is selectively placeable in communication with a selected target of the body of the subject.

The improvements of the present invention further include a system for controlling the glycemic state of a subject comprising a housing device configured to contain at least one chamber; a clock mechanism with a time output, the clock mechanism configured to cooperatively provide logging and/or circadian information to a hereinafter described processor, one or more sensors and sensing modalities associated with the hereinafter described processor, the one or more sensors configured to sense one or more conditions of the subject at one or more sites of the subject and to responsively provide one or more signals corresponding thereto to the hereinafter described processor; a processor contained in the housing device, the processor configured to receive the time output from the clock mechanism and to analyze the one or more signals received from the sensors, wherein said analysis comprises determining at least one feature signal of the one or more signals in a moving time window, and comparing the values of the at least one feature signal to previous values of the at least one feature signal or to a predetermined threshold of the subject in order to detect changes in the at least one feature signal that is indicative of an undesirable glycemic state of the subject; a first reservoir separately containing at least one type of insulin; a second reservoir containing a neuroprotective agent; and an output mechanism configured to deliver a selected one of the separately contained at least one type of insulin of the first reservoir to at least one therapy target of the subject, and in the event of a detected undesirable glycemic state, to deliver the neuroprotective agent of the second reservoir to the subject.

The improvements of the present invention additionally include a method for preventing or correcting the occurrence of undesirable or pathological changes in blood, plasma or tissue glucose of a subject or for protecting the brain of the subject from transient or permanent deleterious effects of hyperglycemia and hypoglycemia, the method comprising the steps of measuring glucose concentrations as a function of time and state in at least two body compartments of the subject; determining thresholds for hypoglycemia or hyperglycemia using glucose concentrations obtained from measuring glucose concentration in the at least two body compartments of the subject; determining neuroglycopenic thresholds by statistically correlating changes in at least one measure of cognitive performance from measuring the glucose concentrations measured in the at least two body compartments of the subject; instituting corrective measures for the subject if the glucose concentrations measured in the at least two body compartments of the subject are, or show a trend indicative of, a transition toward an abnormal or undesirable glucose concentration in the subject; and instituting protective measures for the subject if the glucose concentrations measured in the at least two body compartments of the subject are, or show a trend indicative of, a transition toward an abnormal or undesirable glucose concentration in the subject.

PRINCIPAL OBJECTS OF THE INVENTION

The principal objects of the present invention include: providing a system or method for monitoring or controlling a glycemic state in a subject; providing such a system or method that includes at least one housing device; providing such a system or method that includes one or more sensors capable of producing a signal output; providing such a system or method that includes a reservoir containing one or more types of insulin; providing such a system or method that includes an injection mechanism to release the one or more types of insulin into the subject; providing such a system or method that includes a reservoir containing a neuroprotective agent; providing such a system or method that includes a control mechanism with a processor for receiving and analyzing the signal outputs from the sensors and to cause insulin and/or the neuroprotective agent to be released into the subject; providing such a system or method that is capable of extracting a specimen from the subject for analysis; providing such a system or method that is capable of extending one or more sensors into, and retracting one or more sensors from a subject; providing such a system or method that is capable of extending one or more catheters into, and retracting one or more catheters from a subject; providing such a system or method that is capable of alternating the use of a sensor and/or catheter; providing such a system or method that includes an internal analysis chamber; providing such a system or method that includes a cleaning chamber for cleaning a sensor and/or catheter; providing such a system or method that includes a calibration chamber; providing such a system or method that includes a replacement sensor chamber; providing such a system or method that includes prevention means for preventing the deposition of unwanted substances on the sensors; providing such a system or method that includes removal means for removing unwanted substances from the sensors; providing such a system or method that is capable of monitoring differences in glucose concentration and/or glucose clearance, or indices related thereto, at different sites in the subject; providing such a system or method that includes a warning mechanism; providing such a system or method that includes an algorithm that is adaptive to individual glycemic state characteristics of the subject; providing such a system or method wherein adaptation of the algorithm can be online or offline; providing such a system or method that includes a real-time clock and non-volatile memory for storing and logging information processed by the system in regard to the subject; providing such a system or method that is capable of detecting failure of one or more components of the system; providing such a system or method that includes external components and wired and/or wireless communication links therewith; providing such a system or method that is externally dynamically programable; providing such a system or method for preventing or correcting the occurrence of undesirable or pathological changes in blood, plasma or tissue glucose of a subject or for protecting the brain of the subject from transient or permanent deleterious effects of hyperglycemia and hypoglycemia; and generally providing such a container that is reliable in performance, capable of long lasting life, and particularly well adapted for the proposed usages thereof.

Other objects and advantages of this invention will become apparent from the following description taken in conjunction with the accompanying drawings wherein are set forth, by way of illustration and example, certain embodiments of this invention.

DETAILED DESCRIPTION OF THE PREFERRED EMBODIMENT

Figure 1:
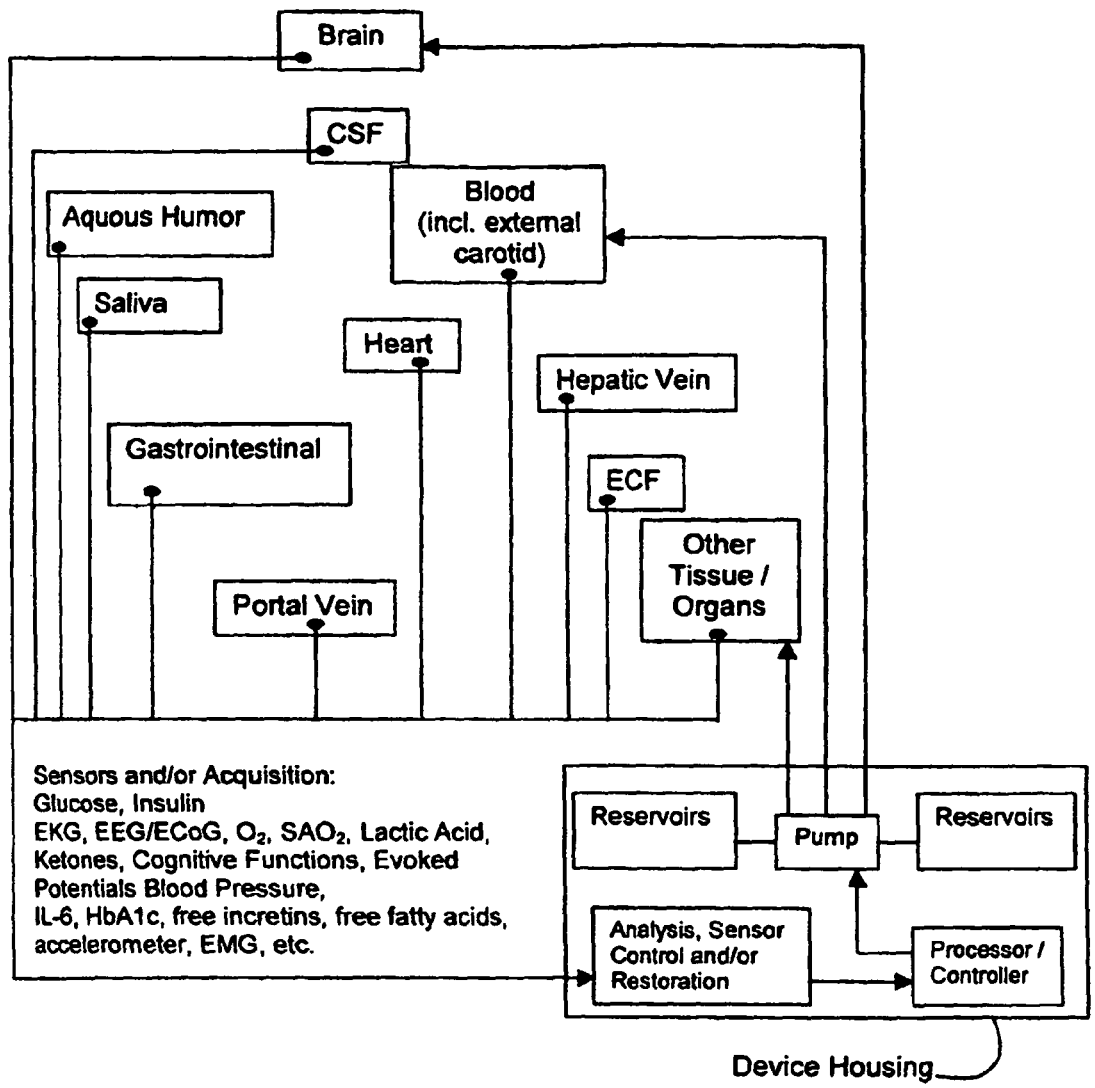
FIG. 1 is a schematic representation of a closed-loop system for implantable glucose monitoring and control of a glycemic state of a subject, wherein communication may be wired or wireless, according to the present invention.

As required, embodiments of the present invention are disclosed herein, however, it is to be understood that the disclosed embodiments are merely exemplary of the invention, which may be embodied in various forms. Therefore, specific structural and functional details disclosed herein are not to be interpreted as limiting, but merely as a basis for claims and as a representative basis for teaching one skilled in the art to variously employ the present invention in virtually any appropriately detailed structure.

The subject invention overcomes the limitations of prior art described above and provides a significant advance in implanted glucose monitoring and control of glycemic state in humans or animals (including diabetes and hypoglycemia) by closely mimicking the physiological process of glucosensing and gluco-regulation, utilizing a certain beneficial degree of redundancy and complementary information, and combining several diverse state-of-the-art technologies in an innovative and novel manner. The invention provides advances in what, where, when, and how to measure information to increase its relevance, and provides a system and method to use this information in an intelligent manner to monitor and control glycemic state. Moreover, the stigma and inconvenience associated with external systems can be overcome through the use of a fully implanted system.

Improved Accuracy and Longevity of Measurements

The method and system described herein makes use of an implantable housing device (preferably a cranial or other osseous mount, e.g., affixed to a rib, but could be attached to the abdominal wall, or pectoral or other mount, provided the device is anchored/stabilized relative to blood vessels/stream and other tissues/organs used as sensor targets) as described in U.S. Pat. No. 6,560,486 to Ivan Osorio et al issued May 6, 2003, which disclosure is incorporated herein by reference. This housing device contains chambers, including an internal analysis chamber, byproduct storage chamber(s), reservoir for insulin (for closed-loop system), reservoir for neuroprotective compounds, substances that promote gluconeogenesis or glycogenolisis, or decrease insulin resistance, or substances that may be used to promote accurate measurements of glucose (e.g., oxygen), possibly a chamber holding replacement sensors, and a sensor cleaning and/or calibration chamber.

In one embodiment of the invention, accuracy and longevity limitations of implanted sensors are significantly improved by designing the sensors so that they can be extended and retracted into and out of the target area for monitoring (e.g., blood), in order to reduce time spent in contact with body's immune system and other substances that may negatively impact its reading and half-life. This feature also reduces or eliminates problems of clotting or significant obstruction/disruption of blood flow. Between extensions into tissue, sensors may be cleaned (removing unwanted materials/substances deposited on the sensor, and/or replaced with a fresh sensor from a refillable supply stored internally to the device. Retractability may also apply to catheters for collection of fluids, blood, etc. and/or for delivery of insulin, glucose or any other substances). The sensor or catheter extensions/retractions, as well as moving of the catheter or sensor into or out of the cleaning chamber can be accomplished via microelectromechanical (MEMS) devices, nanodevices, other mechanical means (e.g., a step up micromotor), molecular means (e.g., via molecular "motors"), magnetic means, or even using gravity. Unwanted substances can be removed from a sensor using a variety of means known to one skilled in the art and Including, but not limited to, chemical treatment, ultrasound, or electrical means. Additionally, deposition of unwanted substances on a sensor is prevented by: (1) limiting exposure to blood/immune system; and/or (2) placing sensors in sites with minimal immune surveillance (e.g. CSF). Additionally, this problem is obviated by measuring glucose indirectly (e.g., by measuring electrical activity from certain relevant locations). The sensor or catheter extensions and retractions may occur through a self-resealing membrane. When the application requires prolonged exposure of the sensors or catheters to body fluid/tissues, physical/mechanical or chemical means may be used to safely prevent deposition of unwanted substances/materials or remove them if deposition has occurred. Another alternative when prolonged or continuous sensor exposure to blood or body fluids is required is to alternate or "multiplex" the exposure of sensors or therapy delivery elements by retracting each one (for cleaning/maintenance or replacement) after a prespecified period of time or as soon as performance begins to deteriorate. Deterioration of a sensor can be determined or predicted in several ways including, but not limited to, calibration testing, expiration of some prespecified duration of expected useful life, or via quantitative analysis of signals obtained from the sensor. For example, the system may include a chamber containing a solution with known glucose concentration, which can be sampled/tested with a sensor intermittently in order to determine whether readings are correct or, if not, to correct for drifts In the measurement process. Alternatively, the system may be configured to include a calibration process in which the user may inject a fluid with known glucose concentration near the sensor and determine whether or not actual readings properly coincide with expected values. Deterioration of the catheter performance can be determined or predicted using similar means, as well as by measuring throughput or flow rate to detect occlusion. These features of the invention minimize unnecessary exposure to immune surveillance and body fluids/metabolic byproducts, lengthening sensor life, and extend the period of accurate sensing, which had previously been limited to a few days of non-degraded performance.

Another embodiment of the invention utilizes intracranial placement for the sensors (e.g. into cerebrospinal fluid), directly away from blood vessels, to markedly decrease exposure to immune surveillance.

A Multisite, Multisensor, Multimodality, Multifactorial Approach

As mentioned above, a limitation of several prior art methods for glucose sensing is that electrode readings are often subject to movement-induced artifacts and other associated measurement noise that adversely affects sensitivity and specificity. Moreover, certain system designs may be prone to failure due to mechanical stresses and sensor movement. We remove this limitation via a multi-sensor approach (enabling redundancy and comparative determination of sensor inaccuracy and/or failure) including incorporation as needed for non-electrode-based readings (e.g., via optical sensing or using other sensor modalities described herein), and embedding the device and/or its sensors into tissue to decrease movement artifacts.

The present invention provides the ability to rapidly (e.g., in real-time) and accurately track temporo-spatial fluctuations in glycemic state, decrease the amplitude of glucose concentration oscillations, and prevent the state from reaching the hypoglycemic/neuroglycopenic and hyperglycemic thresholds by utilizing a multisensor, multisite, multimodality, and/or multifactorial approach. The term "multifactorial" is used to characterize an approach that takes into account among other things:

(1) existence of several compartments with different glucose kinetics and the importance of monitoring those compartments in accordance with said kinetics for accurate characterization of their behavior;

(2) internal (e.g., circadian rhythms; state of glucoregulatory response) and/or external (e.g., time and amount/type of food intake; physical activity) factors;

(3) importance of establishing hypoglycemic, neuroglycopenic and hyperglycemic thresholds on an individual basis and of updating as needed to accurately track their status/evolution since the disease process and internal and external factors/conditions vary with time;

(4) that diabetics may lose the ability to recognize they are becoming hypoglycemic/neuroglycopenic and once they are neuroglycopenic that they become confused and unable to behave adaptively or in a self-protective way;

(5) that neuroglycopenia can be detected only by measuring indices of brain functions; and (6) that prevention of neuroglycopenia and protection of the brain (the most sensitive body organ to rapid changes in glucose concentration) from its deleterious effects requires acknowledgment of above listed factors and automated real-time implementation of the steps/operations required to carry them out to allow automated control of glucose, warning of impending or established hypoglycemia or hyperglycemia and protection of the brain from their effects.

One embodiment of the invention incorporates multiple metabolic, electrical or other types of sensors, which may be located at multiple sites, to account for differences in glucose concentration and consumption rates and monitor, if relevant, the site's functional state. Preferably, measurements from two or more sites/compartments and modalities (e.g., metabolic and electrical) are performed simultaneously (or in a temporally synchronized manner to account for temporal differences between measurements) to allow for more precise and timely detection, prevention, or control of undesirable glycemic state fluctuations. Preferred sensing sites include but are not limited to, portal/hepatic circulation including intraparenchymal recording from liver, external carotid and vessels/compartments with high blood flow rate and high tolerance for embolization and also from intracranial structures such as the brain. The embodiment also utilizes a multifactorial approach to identification and control of glycemic state in a physiological framework that may include monitoring one or more autonomic indices (such as hormonal or electrical) and/or cerebral indices (such as electrical or cognitive signals and glucose concentration) for individualized adaptive control.

In another embodiment, the sensing process/glucose analysis is performed within a compartment of the device itself. The blood or target tissue in which to assess glucose concentration may be sampled and isolated from the immune system prior to introduction of a sensor, thereby isolating the sensor system from effective immune system surveillance or attack. In this case, the system may include at least one micro-needle or catheter that is inserted into at least one target (e.g., artery or other tissue or organ—see, e.g., FIG. 1) and is used to acquire a small sample that is then analyzed for the concentration of at least one substance, for example, glucose and/or insulin. This design retains the benefits of microdialysis but does not require the process to be carried out externally to the body. Byproducts from the analyses that cannot be safely diffused back into the body or ablated may be stored within a chamber that can be periodically emptied by external access through a port, as described in U.S. Pat. No. 6,560,486 to Ivan Osorio et al issued May 6, 2003, which disclosure is incorporated by reference herein. This transfer from the internal analysis chamber to storage chamber can be accomplished by means of a valve that is placed between these two chambers to allow unidirectional flow (from Internal analysis to byproduct storage chamber only). Transfer may be active, for example, using microfluidics or microelectromechanical (MEMS) devices, or by pressurizing the internal chamber. Alternatively, transfer may be passive, for example, utilizing a semi-permeable membrane, chemically-activated membrane, hydrostatic pressure (by allowing a certain volume to accumulate in the internal chamber), gravity, or any combination thereof. In the case of gravity, the internal chamber is equipped with at least two outlets, one vertical and operative with subject standing up or sitting and the other orthogonal to it and operative with subject in recumbent position (in both dorsal an ventral positions), allow through a valve, drainage of by-products into the appropriate chamber. Another possibility to drain the internal chamber by gravity is through a device resembling a gyroscope fitted with a pendulous weight or some equivalent to induce precession due to gravity.

External access to chambers, to remove byproducts or replenish reservoirs, can be obtained via one or more ports that allow access from the exterior into the different chambers in a manner similar to that used to replenish the reservoir of an Implanted drug pump. Other means for external access are disclosed in U.S. patent application Ser. No. 10/240,289, filed Sep. 14, 2004 and which is incorporated herein by reference.

The actual glucose analysis process can be electrochemical, optical (including, but not limited to optical absorption, spectroscopy, polarimetry, fluorescence, and spectrophotometry), or any other method known to one skilled in the art that may be sufficiently miniaturized and suitable for housing within an implantable device. One skilled in the art will appreciate that other indices relevant for monitoring glycemic state of the subject may be measured and monitored in a similar manner, including local insulin levels, osmolality, glucosuria, and concentrations of other substances in plasma, blood, or tissue including, but not limited to, blood oxygen levels, ketones (produced when brain doesn't get enough glucose), interleukins (e.g., IL-6 may serve as a type of carbohydrate sensor), lactic acid, free incretins, free fatty acids, Hb1Ac (glycated hemoglobin), epinephrine, cortisol, glucagon, and neurotransmitters or neuromodulators. Additionally, firing patterns of various neurons in the brain and/or body (e.g., glucose-responsive (GR) neurons from hypothalamic nuclei, which play a role in the regulation of feeding and satiety) may be monitored to gain real-time/instantaneous information about the glycemic state of a subject.

In addition to measuring glucose concentrations from blood samples, the system can also obtain sensor readings of glucose concentration, as well as measurements of neuronal electrical activity, and/or other types of sensors placed in brain, cerebrospinal fluid (CSF), extracellular fluid (ECF) and other tissue or organs to account, in an encompassing way, for differences in glucose kinetic behavior and consumption rates. Moreover, the complementary (and possibly redundant) information provided by the various sensor types and placement configurations utilized in this invention result in increased accuracy and robustness of glycemic state measurement and enables more accurate monitoring, adverse event warning/logging, and glycemic state control. These measurements from other locations in the body can be used together with those obtained directly from blood to gain additional information regarding the overall glycemic state of the person being monitored.

Other potential placements for glucose sensors (and/or other sensors, e.g., insulin) to obtain information that could be useful in monitoring overall glycemic state and its evolution include, but are not limited to:

(a) gastrointestinal tract including, but not limited to the mouth (e.g., affixed to the hard palate), esophagus, or small intestine to monitor sugars and/or carbohydrates as consumed and/or present in the saliva, (b) in/over the eye, e.g., glasses, contacts, or a sensor implanted within the eye to monitor glucose in aqueous humor (see, e.g., U.S. Pat. No. 5,535,743 to Jurgen Backhaus et al, issued Jul. 16, 1996), (c) in the portal vein to monitor glucose absorption (absolute and/or relative) and absorption rate in the intestines, thereby obtaining an early indicator of glucose inputs into the system, (d) in the hepatic vein to monitors glucose output from liver, (e) around, over, or inside the carotid system (e.g., external carotid or branches such as the temporal middle meningeal) providing an accurate representation of glucose supplied to the brain, (f) monitoring glucose concentration directly from the brain or CSF or indirectly by monitoring the electrical activity of glucosensing neurons (glucoresponsive or glucose-excited and glucosesensitive or glucose-inhibited) including but not limited to those located in hypothalamic nuclei (e.g., ventromedial, arcuate, lateral), motor cortex, hippocampus, amygdala, septum, striatum, locus coeruleus, nucleus of the solitary tract, dorsal vagal complex. The activity of these neurons may be also monitored through measurement of neurotransmitters such as neuropeptide Y, cholecystokinin, pro-opiomelanocortin, glutamate, GABA, nor-epinephrine and dopamine among others. Detection of changes in glucose concentrations by measuring the electrical activity of brain glucosensing neurons provides important advantages over optical or chemical sensors: (i) High sensitivity; glucosensing neurons are able to detect changes in glucose concentration of as little as approximately 0.1-0.15 mM/L; (ii) Considerably longer half life since electrodes are made from noble metals which last for decades; and (iii) Ability to monitor changes in glucose concentration continuously and in real-time. Moreover, detection of unsafe changes in glucose concentrations by measuring the electrical activity of selectively vulnerable neurons is highly useful. Recording and analysis may be made from spontaneous (background) or evoked electrical activity at venous scales (single cells; small neuronal aggregates, etc). This activity may be recorded not only intra—but also extracranially; see, U.S. patent application Ser. No. 10/622,238 to Ivan Osorio et al, filed Jul. 18, 2003, which disclosure is incorporated by reference herein in its entirety.

(g) The activity of glucosensitive elements (putative glucose biosensors) in the portal vein, gastrointestinal tract or carotid body.

Additionally, the system may include sensors that obtain other complementary information relevant for determining glycemic state and its evolution, including physical activity state (obtained, for example, using accelerometers, heart rate, sweat, body temperature, and/or EMG), information about the sleep-wake cycle (to account for circadian influences and because this may impact warning and control outputs) emotional state (obtained, for example, from heart rate and manual external inputs), other hormonal changes (e.g., menstrual, which may be measured using hormone sensing techniques, user input, or calculated according to a calendar), weather (obtained, for example, from external temperature, barometric, humidity, and other sensors). The system may also include an external user interface component that allows the user to enter information such as time from or to expected or actual food consumption, food type/glycemic index, and other information useful for control, diagnosis, or monitoring. The system may also include extracorporeal sensors that automatically or semi-automatically log information about the time, composition and amount of dietary intake or subject activity which is input to the main device processor/controller to help estimate dose, timing and rate of delivery of insulin. Other useful markers include measurements of attention or other cognitive markers, and electrophysiologic markers that serve as bioindices of brain glucose concentration, e.g., EEG, evoked potentials, and automated measures of attention. The additional information obtained by these measurements can be used as needed to significantly enhance the system's ability to accurately quantify glucose concentration, including its transport from blood to other vital organs (such as brain) and also to provide redundancy of information that makes the system less susceptible to artifacts. Protection against neuroglycopenia can be significantly improved by monitoring brain activity together with local glucose concentration.

Other relevant information that may be obtained via sensors and used in the monitoring, warning, or control functions of the method/system include, but are not limited to, blood flow, blood pressure, and optical monitoring of neuronal activity (obtained, e.g., via near infrared optical observations).

Glycemic State Monitoring and Tracking

As the signal(s) is (are) received into the system, monitoring of glycemic state and detection of abnormal state changes are performed by signal analysis in a processor. This analysis may be digital, analog, or a hybrid. For example, the method for signal analysis described in (1) U.S. Patent Application No. 20030187621 to A. V. Nikitin et al published Oct. 2, 2003, and/or that described in (2) U.S. Pat. No. 5,995,868 to Osorio et al, issued Nov. 30, 1999, both of which disclosures are incorporated herein by reference, provide means for analysis of complex, non-stationary signals such as that of glucose concentration in the brain/body. These methods are capable of detecting small but relevant changes in concentration which may be overshadowed by noise, as well as accounting for drifts and other baseline changes that often take place in nonstationary signals (e.g., via normalization by signal background on an appropriate timescale for the signal being monitored). They accomplish this task by measuring aspects of the distribution(s) of signal features indicative of the glucose-insulin kinetics as these distributions evolve in time, utilizing a time and/or state weighting of information. The monitoring can be adaptive and learn details of dynamics that are specific for the particular subject as time evolves (e.g., utilizing exponential forgetting) to further improve efficacy with time.

While measurements from different sensors and placements each have associated delays with respect to glucose absorption and availability for consumption, their combined information, appropriately weighted, provides more meaningful information about the state of glucose metabolism including glucose reserves (glycogen) which can be incorporated into a model that allows more physiologically-desirable delivery of insulin and consequently, better and safer control. Statistical methods, such as those developed by Hurst, may be applied to this end.

Prior art methods and systems for glycemic state control do not adequately incorporate into glucose control models or strategies the relative or partial dependency of glucose concentration at time, $t_0$, upon its concentration at a previous time, $t_{-1}$. Incorporation into the control strategy of other factors that influence glucose concentration, such as food intake or energy expenditure between $t_{-1}$ and $t_0$ and the circadian variations in putative glucoregulatory mechanisms and insulin sensitivity, can further improve glycemic control in diabetic persons.

There are many mathematical models describing the glucose-insulin interactions in the body (see, e.g., Bartolozzi et al., European Journal of Operational Research 121 (2000), 435-466.) and these models include a number of parameters (e.g., insulin sensitivity index) that, if accurately estimated and tracked as they evolve in time, would enable very effective control of glycemic state and prevent unwanted hyperglycemia and hypoglycemia. Identification and tracking of such (potentially time-varying) parameters as they evolve can be achieved using appropriate mathematical techniques such as time and state-weighted least squares as described in M. G. Frei, Parametric Identification in Continuous-Time Stochastic Systems Using Time and Space Weighted Least Squares, Ph.D. dissertation, University of Kansas, Lawrence, Kans., 1993, the state may be estimated using well-known techniques such as Kalman filtering, and changes can be found using techniques described U.S. Patent Application No. 20030187621 to A. V. Nikitin et al published Oct. 2, 2003, and U.S. Pat. No. 5,995,868 to Osorio et al, issued Nov. 30, 1999.

The incorporation of an implanted monitor to track glycemic state enables the system to acquire and learn important individualized information from the subject regarding their own processing of glucose and the glucose-insulin interaction, and to update this information as the dynamics change with time and state. In particular, the response to, for example, a bolus of rapid-acting insulin can be monitored and used to adapt model parameters for use in adaptive prediction and control, enabling determination of optimal (or near-optimal) dosage level and timing for use in controlling the state. The sensor information sampling frequency and processing/analysis of chemical or physical signals (including thermal) may be adjusted/adapted according to the prevailing alimentary state of the subject. This is particularly relevant for two of these states: a) Prandial and immediate post-prandial during which the risk for hyperglycemia is highest, and b) Basal or postabsorptive during which subjects are at highest risk for hypoglycemia and neuroglycopenia. Intensive monitoring and highly active control are necessary in or near both of these states to prevent the subject from reaching (or, if reached, to minimize time spent in) both of these states. Additionally, glycemic state may be sampled more frequently when state estimates are closer to an undesirable state or when there is a significant change between the most recent reading and previous readings, and less frequently when readings are relatively stable and within a desired range.

An important factor in effective control of glycemic state includes determination of hyperglycemic and hypoglycemic thresholds that may be time and state dependent. In the subject invention, these may be estimated and/or tracked as they change, incorporating measurements/assessments of the gluco-regulatory response of the subject into the threshold determination and, more generally, in determining undesirable glycemic state(s). The gluco-regulatory response can be classified as intact or impaired. In the case of intact response, physiological and/or hormonal markers may be used to determine activation associated with undesirable hypoglycemia. These markers may include measurements of heart rate (e.g., tachycardia), skin resistance, and/or perspiration. In the case of impaired gluco-regulatory response, statistical thresholds may be used together with cerebral markers including cerebral (e.g., attention measures) and electrophysiological markers (e.g., EEG, or evoked responses such as P300). Estimation of the Hurst parameter may also be used to anticipate undesirable swings in plasma or brain glucose concentrations and institute appropriate automated control measures.

Control of Glycemic State and Warning of Adverse Events

Another embodiment of the invention uses different insulin formulations (rapid acting, intermediate acting, long acting, liposomes) or of other glucose-lowering agents at different times or simultaneously in different proportions. and through different routes (e.g., blood, respiratory). Adjust rate and timing of delivery (in relation to carbohydrate load to maintain peak and nadir glucose concentrations within physiologic limits;

Another embodiment of the invention provides automated warning of impending (or occurring) hypo- or hyperglycemia so that the subject may take preventative steps or if necessary, so that the system may automatically institute corrective and/ or neuroprotective measures. These may take place at pre-specified concentrations such as when plasma glucose concentration approaches approximately 3.6-3.8 mM/L, concentrations, at which hypoglycemic symptoms appear if awareness is not impaired, and before brain glucose uptake begins to decline (at plasma glucose of approximately 3.6 mM/L), both of which occur before cognitive function begins to deteriorate (plasma glucose of approximately 2.7-3.1 mM/L.); if hypoglycemic awareness or the counter-regulatory response are impaired, automated warning, neuroprotective and corrective measures can be instituted and controlled using measures of glucose concentration or of neuronal or cognitive activity. The ability of the analyses to quantify glycemic state (including temporal and spatial or sub-compartment changes) allows the method and/or system to issue graded warnings dependent upon intensity, duration, spread, or other severity measures of the detected undesirable state(s).

As mentioned above, the decisions and procedures for glycemic control in commercially available systems are entirely in the hands of the diabetic person who may suffer from hypoglycemic unawareness, which makes them incapable of using the control method or system to correct this serious and potentially harmful situation. This is a fundamental flaw in prior art that can be overcome only through automated warning of impending hypoglycemia and, when necessary, automated correction. For example, if a hypoglycemic warning is issued and glucose concentration does not rise within a prespecified time (because the patient or caregiver did not take appropriate action), a carbohydrate, a compound that promotes glycogenolysis or an energy equivalent substrate, may be automatically delivered to improve glycemia.

Another embodiment of the invention utilizes glycemic state-based nerve stimulation in order to automatically enhance either parasympathetic activity (e.g., by stimulating the vagal nerve) to avoid or reduce hyperglycemia, or sympathetic activity (e.g., by stimulating the splachnic nerve or ganglion or celiac ganglion) to abort or reduce duration and intensity of hypoglycemia.

In addition to accurate real-time monitoring of glycemic state, the system can be equipped with a processor and a control algorithm (that may be adaptive to subject's individual glycemic state characteristics) used to automatically control insulin delivery in real-time to the subject to prevent hyperglycemia and hypoglycemia or other undesirable states. The algorithm adaptation may occur online and/or offline and can incorporate information obtained from monitoring and subject response to the control algorithm. This system may contain reservoirs or chambers that can contain long, short, and/or rapid acting insulin types that may be delivered to the body via catheters, needles, diffusion through pores, etc. It may also be equipped with a sensory stimulus used to warn the subject of abnormal or undesirable glycemic states and/or state changes. The warning may include a message indicative of actions that should be taken by the user and/or caregiver in response to the system event detection such as, for example, telling the user to ingest a certain amount of carbohydrates immediately. The system may also be equipped with a real-time clock and non-volatile memory to store or log information regarding detection of adverse events as well as the start, end, and intensity or other relevant features of particular states of interest. Use of adaptive prediction (e.g., as described by M. G. Frei, Parametric Identification in Continuous-Time Stochastic Systems Using Time and Space Weighted Least Squares, Ph.D. dissertation, University of Kansas, Lawrence, Kans., 1993) together with measured responses to insulin dosing enables the system to accurately control glucose concentration and maintain it within normal/desirable levels.

One skilled in the art will appreciate that the system may contain an external component that may be communicatively connected to the implantable portion of the system and may communicate by, e.g., telemetry in order to program the internal device, receive information externally for review, monitoring, warning, and/or treatment purposes, etc. For example, the external system may call "911" in the event of significant hypoglycemia, or administer cognitive testing of the subject to determine their state of awareness. Cognitive changes indicative of impending neuroglycopenia or of established neuroglycopenia may be identified by administering cognitive tests to the subject. For example, complex attention tests may be automatically triggered at times when the subject is at highest risk for neuroglycopenia (e.g., during the postabsorptive period), or following insulin administration, or when glucose concentration approaches or reaches the hypo- or hyperglycemic thresholds, or at some other prespecified or random time intervals. For example, the tests may be auditory, delivered by a recorder and the answers may be verbal and recorded for on-line or off-line analysis. For example, latency (in seconds) from questions to answers and number of correct responses during euglycemia may be quantified and analyzed to obtain a baseline for each individual against which valid statistical comparisons may be made. Significant increases in latency or decreases in the number of correct answers for a given individual may indicate impending or established neuroglycopenia (depending on the magnitude of the changes) which automatically triggers warning, corrective and/or protective actions. Moreover, the implanted system may include wired, fiber optic, or wireless communication between the sensors (sensing elements) and the portion of the system containing a processor, reservoirs, and control system. The system may be externally programmable to accept externally obtained glucose measurements that may, for example, be utilized in the calibration of implantable sensors. The device may include additional features to prevent failure as disclosed in Provisional Patent Application No. 60/518,027 to Ivan Osorlo et al, filed Nov. 7, 2003, which disclosure is incorporated herein by reference in its entirety.

Substances which promote glycogenolysis or gluconeogenesis (in the face of hypoglycemia), entrance of glucose into cells and glycogen formation and block gluconeogenesis may be injected/infused into one or more sites, including but not limited to delivery directly into arteries (e.g., external carotid), intraperitoneal area, directly into the portal vein, directly into the brain, or to any other tissue. This minimizes delay to action (currently a problem with typical subcutaneous injections). A large part of the inherent difficulties with diabetes management arises from the delay (and variability) between time of food consumption to corresponding glucose concentration rise, as well as the delay between insulin injection and peak effect. These problems are overcome by the subject invention through the use of (possibly multiple) elements for sensing useful information along with the use of (possibly multiple) elements for insulin delivery, or of modalities that mimic the physiological release into the bloodstream. For example, the release of insulin may be pulsatile or phasic (Butler P. Pulsatile Insulin Secretion. Novartis Found Symp 2000; 227:190-199; discussion 199-205. Nesher R, Cerasi E. Modeling Phasic Insulin Release: Immediate and Time-Dependent Effects of Glucose. Diabetes 2002; 51: Suppl 1:S63-59) or modulated by the kinetic of its disappearance from plasma (Thorsteinsson B. Dan Med Bull 1990; 37:143-153). The control system may utilize more than one type of insulin formulation (e.g., rapid acting and long acting) to enable better glycemic state control. Rapid acting is the preferred type for immediate control of hyperglycemia, especially when delivered directly into the blood or intraperitoneal area. Long acting formulations may be used to control more slowly fluctuating baseline glucose levels and maintain desired state. Additionally, prior art does not provide means of automatically protecting the brain from the deleterious effects of hypoglycemia on selectively vulnerable neuronal populations. Automated release into the blood stream, CSF, or brain of neuroprotective compounds or anti-seizure agents will be performed, to decrease the risk of neuronal damage in the event of hypoglycemia. FIG. 1 shows a schematic illustration of the closed-loop system for control of glycemic state.

A mathematical description of the multisite, multisensor, multimodality, multifactorial approach to glycemic state monitoring and control as disclosed herein may be stated as follows:

(1) Let X(t) be the "glycemic state" of the subject at time t. We can denote individual components of glycemic state as $X_{ij}(t)$, where index i is indicative of a sensor site (or subcompartment) and index j indicates the sensor or signal type. For example, j=1 may indicate local glucose concentration, j=2 may indicate local insulin concentration, etc., while i=1 may indicate portal vein, i=2 may indicate external carotid artery, and i=3 may indicate brain CSF.

(2) Let $Y_{ij}(t)$ denote the measurement of the state component $X_{ij}$ taken at time t, and Y(t) the set of all observations made at time t. We can estimate the state vector based on available (and typically noisy/imprecise) observations using, for example, Kalman filtering, to obtain the state estimate $X_{hat}(t)=E(X(t)|Y(s), s<=t)$.

The control process used by the system can, for example, take the form of a model reference adaptive controller, in which the control input $U(t)=[U_{ij}(t)]$ (i.e., the control at time t consists of Inputs indexed by site and input type—for example, a bolus of fast or slow-acting insulin) is selected in order to minimize the distance (according to a suitable and likely component and time-weighted norm) between $X_{hat}(t)$ and a desired reference trajectory $X_r(t)$. The selected control inputs may, for example, be those inputs that (based on estimated impulse response of the system) minimize the expected distance between the state estimate and the reference trajectory at the next point in time (i.e., that control which optimizes tracking of the desired glycemic state. The vector difference between $X_{hat}(t)$ and $X_r(t)$ can be analyzed in terms of magnitude and direction as it evolves and the time and/or state-weighted distribution of the distance can be quantified to assess functional glycemic state and enable detection, warning, logging, and automated control to avoid hypoglycemic states, neuroglycopenic states, hyperglycemic states, or any other undesirable glycemic state.

Figure 2:
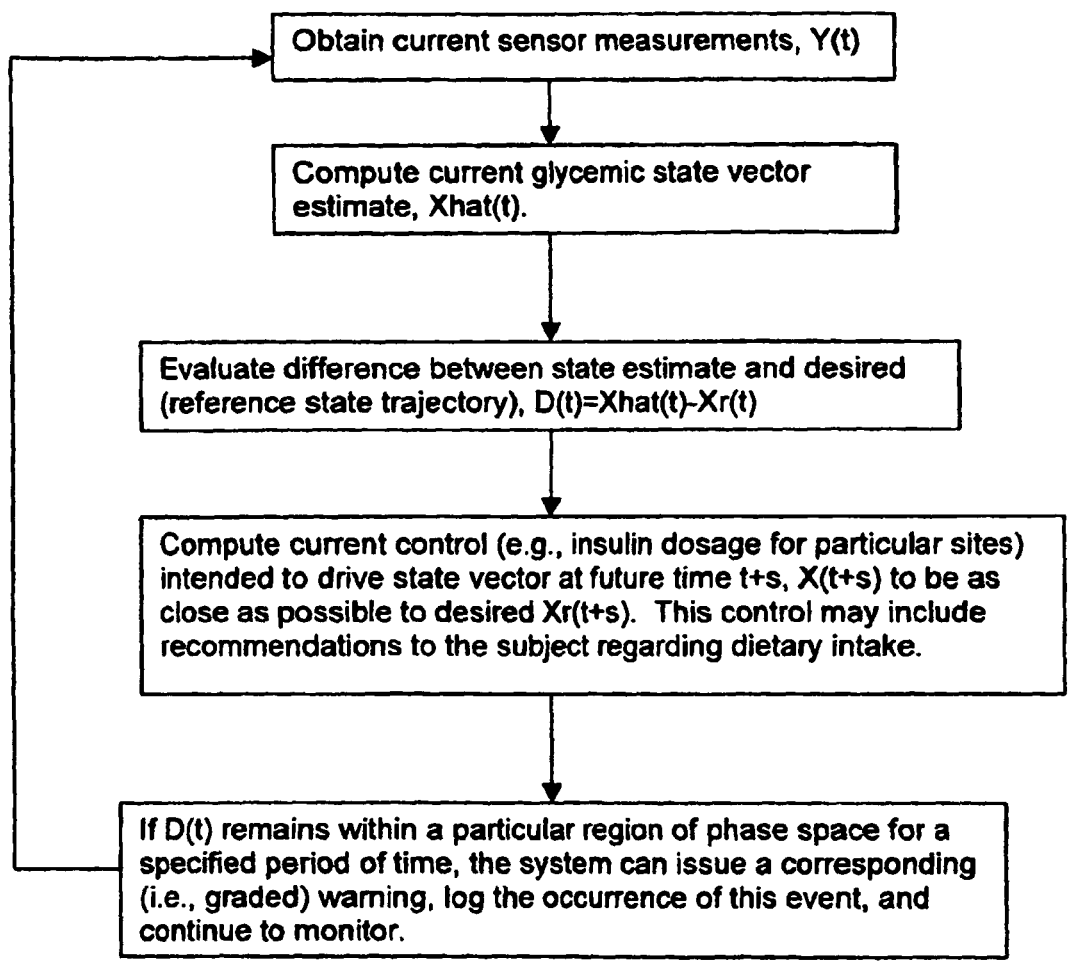
FIG. 2 is a flowchart for a system for glucose monitoring and control of a glycemic state of a subject, according to the present invention.

For purposes of illustration, a simplified flowchart describing one such embodiment of the monitoring and control process is presented in FIG. 2.

Certain differences (and their temporal evolution) between the available state estimate and the desired state trajectory may be determined to correspond to hyperglycemic, hypoglycemic, or neuroglycopenic thresholds. When these are reached, the system may adjust automated control measures to begin various automated therapies including infusion of glucose, glucagons, or other substances that modify glycogenolysis or gluconeogenesis, or delivery of neuroprotective agents to vulnerable sites/neuronal populations. These differences can also be used to produce a graded warning (which may be based in part upon subject state: differing, e.g., between awake and asleep with the latter or non-response to low-level warning resulting in automated intervention and higher grade/intensity of warning). Detection of more serious states could more rapidly result in automated therapy steps, including delivery of neuroprotective agents.

Additionally, if vector D(t) results in larger than desired difference between desired and measured glycemic states, the system may utilize additional state sensors to improve reliability and redundancy of state estimates. This strategy allows efficient system performance using a small number of sensors provided that the monitoring and control cause the state to remain suitably stable and near the desired reference trajectory, but allows more intensive measurement and control when the state deviates from desired ranges.

It is to be understood that while certain forms of the present invention have been illustrated and described herein, it is not to be limited to the specific forms or arrangement of parts as described and shown.

What is claimed and desired to be covered by Letters Patent is:

1. A system for monitoring and/or controlling a glycemic state of a subject, the system comprising:

(a) at least one housing device adapted to be fully embedded internally within a subject wherein the at least one housing device includes:
  (1) a self-sealing membrane,
  (2) one or more sensors configured and adapted to produce a sensor output relating to a glycemic state wherein each of the one or more sensors is extendable through the self-sealing membrane into, and retractable back through the self-sealing membrane from being in, direct contact with a target of a subject,
  (3) a reservoir containing insulin and having an output port,
  (4) an injection mechanism configured to controllably inject the insulin through the output port,
  (5) a control mechanism configured to:
    (A) receive at least one sensor output from the one or more sensors,
    (B) obtain at least one measurement of cognitive performance of the subject,
    (C) analyze the at least one sensor output to detect an impending or occurring hypoglycemia and/or hyperglycemia condition and correlate the at least one sensor output with the at least one measure of cognitive performance to determine the presence of an impending or occurring neuroglycopenia, and
    (D) responsively control the quantity of insulin injected through the output port by the injection mechanism; and
  (6) an insertion mechanism controlled by the control mechanism, the insertion mechanism being configured and adapted to selectively extend at least one of the one or more sensors through the self-sealing membrane to be, and to selectively retract at least one of the one or more sensors back through the self-sealing membrane from being, in direct contact with a target of the subject; and
(b) a response mechanism that is activated when the control mechanism detects an impending or occurring neuroglycopenia, hypoglycemia and/or hyperglycemia condition as determined by the control mechanism from the sensor outputs as determined by the control mechanism from the sensor output(s) and measure(s) of cognitive performance; and
(c) wherein the control mechanism is further configured and adapted to automatically cause the sensor extensions and retractions by the insertion mechanism after a predetermined period of time.

2. The system as described in claim 1, wherein the neuroglycopenia is determined using cognitive, EEG, evoked potential, or autonomic function tests; and hyperglycemia or hypoglycemia are determined by measuring the concentrations of glucose in the plasma, blood or tissue of a subject.

3. The system as described in claim 1 wherein, in the presence of neuroglycopenia or hypoglycemia, the response mechanism performs at least one of shutting down insulin delivery, or issuing a warning; or releasing a carbohydrate, a compound that promotes glycogenolysis or gluconeogenesis, an energy equivalent substrate, or a neuroprotective agent.

4. A system for monitoring and/or controlling a glycemic state of a subject, the system comprising:
(a) at least one housing device adapted to be fully embedded internally within a subject wherein the at least one housing device includes:
  (1) a self-sealing membrane,
  (2) a sensor cleaning chamber,
  (3) one or more sensors configured and adapted to produce a sensor output relating to a glycemic state wherein each of the one or more sensors is extendable through the self-sealing membrane into, and retractable back through the self-sealing membrane from being in, direct contact with a target of a subject,
  (4) a reservoir containing insulin and having an output port,
  (5) an injection mechanism configured to controllably inject the insulin through the output port,
  (6) a control mechanism configured to:
    (A) receive at least one sensor output from the one or more sensors,
    (B) obtain at least one measurement of cognitive performance of the subject,
    (C) analyze the at least one sensor output to detect an impending or occurring hypoglycemia and/or hyperglycemia condition and correlate the at least one sensor output with the at least one measure of cognitive performance to determine the presence of an impending or occurring neuroglycopenia, and
    (D) to responsively control the quantity of insulin injected through the output port by the injection mechanism; and
  (7) an insertion mechanism controlled by the control mechanism, the insertion mechanism being configured and adapted to selectively extend at least one of the one or more sensors through the self-sealing membrane to be, and to selectively retract at least one of the one or more sensors back through the self-sealing membrane from being, in direct contact with a target of the subject; and
(b) a response mechanism that is activated when the control mechanism detects an impending or occurring neuroglycopenia, hypoglycemia and/or hyperglycemia condition as determined by the control mechanism from the sensor outputs as determined by the control mechanism from the sensor output(s) and measure(s) of cognitive performance; and
(c) wherein the control mechanism is further configured and adapted to cause the insertion mechanism to automatically:
  (1) extend another at least one sensor through the self-sealing membrane and into direct contact with a target of the subject, and
  (2) retract an at least one sensor from a position wherein the at least one sensor is extending through the self-sealing membrane, back through the self-sealing membrane and into the sensor cleaning chamber with the retracted sensor being retained fully embedded within the subject.

* * * * *